United States Patent [19]

Look et al.

[11] Patent Number: 5,008,542
[45] Date of Patent: Apr. 16, 1991

[54] METHOD AND SYSTEM FOR AUTOMATED MEASUREMENT OF WHOLE-WAFER ETCH PIT DENSITY IN GAAS

[75] Inventors: David C. Look, Dayton; James S. Sewell, Kettering; Millard G. Mier, Yellow Springs; John R. Sizelove, Kettering; Dennis C. Walters, Fairborn, all of Ohio; Scott C. Dudley, Air Force Academy, Colo.

[73] Assignee: The United States of America as represented by the Secretary of the Air Force, Washington, D.C.

[21] Appl. No.: 456,924

[22] Filed: Dec. 20, 1989

[51] Int. Cl.$^5$ .................... G01N 21/88; G01N 21/35
[52] U.S. Cl. .................... 250/341; 250/358.1; 356/30; 356/31
[58] Field of Search ............ 250/341, 358.1; 356/30, 356/31

[56] References Cited

U.S. PATENT DOCUMENTS

| | | | |
|---|---|---|---|
| 4,559,451 | 12/1985 | Curl | 250/560 |
| 4,637,726 | 1/1987 | Walker et al. | 356/367 |
| 4,678,904 | 7/1987 | Saaski et al. | 250/227 |
| 4,740,708 | 4/1988 | Batchelder | 250/563 |
| 4,778,987 | 10/1988 | Saaski et al. | 250/226 |

OTHER PUBLICATIONS

J. S. Sewell et al, Automated and Calibrated Whole Wafer Etch Pit Density Mapping in GaAs, 18 J. Elect Mat'ls, p. 191 (Jan. 1989).
D. C. Look et al, A New Technique for Whole-Wafer Etch-Pit Density Mapping in GaAs, 65 J. Appl Phys. (Feb. 1989).
J. M. King et al, GaAs Material/Device Correlation Study, Wright Research and Development Center Technical Report WRDC-TR-89-5015 Apr. 1989.
P. Dobrilla et al, Distributions of Residual Stress, Dislocations, and EL2 in Czochralski-Grown Semi-Insulating GaAs, J. Appl. Phys., vol. 60, pp. 169-176 (Jul. 1986).
G. J. Rees et al, A Simple Technique to Evaluate the Density of Overlapping Etch Pits in GaAs, Materials Letters, vol. 4, No. 11, 12 (Oct. 1986).
D. C. Look et al, "GaAs Materials/Device Correlation", from Proceedings of the U.S. Conference on GaAs Manufacturing Technology, Portland OR pp. 9-13, Oct. 12-14, 1987.

Primary Examiner—Carolyn E. Fields
Assistant Examiner—James E. Beyer
Attorney, Agent, or Firm—Thomas L. Kundert; Donald J. Singer

[57] ABSTRACT

A method and system for measuring whole-wafer etch pit density ($\rho_D$) is disclosed in which an etch GaAs wafer is tested for fractional transmission at a plurality of points over its surface. The fractional transmission (T) of light through the wafer is detected, amplified and fed to a computer where at least two points of transmission measurement are selected for calibration. From these measurements, together with an estimate of the average etch pit size (area), the values for fractional transmission in regions of low etch pit density $T_O$ and high etch pit density $T_E$ may be calculated, and used to convert transmission data directly to etch pit density ($\rho_D$) according to the equation $$\rho_D = -\frac{1}{a} \ln \frac{T^{\frac{1}{2}} - T_E^{\frac{1}{2}}}{T_O^{\frac{1}{2}} - T_E^{\frac{1}{2}}}.$$

11 Claims, 5 Drawing Sheets

METHOD AND SYSTEM FOR AUTOMATED MEASUREMENT OF WHOLE-WAFER ETCH PIT DENSITY IN GAAS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention relates to GaAs wafers and particularly to a method and system for automated measurement of whole-wafer etch pit density in GaAs wafers.

2. Description of the Prior Art

One of the prime factors affecting large-scale device development in GaAs is the etch pit or dislocation density. Although there is some disagreement on whether or not a single dislocation near a device such as a field-effect transistor (FET) can significantly affect the electrical behavior of that device, there seems to be general agreement that a large number of dislocations within the region surrounding the device will indeed affect its electrical properties. A good way to study such effects is to compare the variations in dislocation density over a large area, such as a 2-inch or 3-inch wafer, with the corresponding variations in some critical device parameter, such as the threshold voltage. Then standard statistical techniques can be used to determine the degree of correlation. Modern autoprobe techniques can be used to map the particular device parameter, even up to many thousands of devices. However, there is no such convenient technique to map the dislocation density. The standard method is to place the wafer in hot KOH, forming small etch pits where dislocations intersect the surface, and then to count the pits within a given area about the point of reference. This procedure is very tedious, so that seldom are more than lo positions analyzed on a given wafer, making good correlation with device properties nearly impossible.

U.S. Pat. No. 4,637,726 discloses a system for mapping GaAs and other semiconductor wafers for areas of nonuniformity. The wafer is positioned in a magnetic field and illuminated by a light source at a plurality of points on the surface thereof. A computer initializes the light level and the electronic gain of each detector preamp associated with a fiber optic link from an analyzer. The magnetic field direction is then reversed by computer command, causing a localized change in intensity cf light passing through the wafer due to Faraday Rotation. The resulting change in detector output together with location and wavelength data can be used to compute a map of the wafer.

U.S. Pat. No. 4,740,708 discloses a system and procedure for the inspection of the surface of a semiconductor wafer which ascertains that particulate contaminants have been adequately cleaned from the surface during the manufacture of integrated electric circuits The wafer is advanced in a first direction and is optically scanned in a second direction, transverse to the first direction, for recording intensities of light reflected normally from the wafer surface as a function of location on the scan line.

However, none of the above references teaches a method or system for obtaining whole-wafer dislocation (etch pit density) maps of a GaAs surface.

SUMMARY OF THE INVENTION

An object of the invention is to provide a method and system for measuring whole-wafer etch pit density in GaAs.

It is another object of the invention to provide an automated, digitized method and system for realizing dense, whole-wafer etch pit maps of a GaAs surface.

According to the invention, an etched GaAs wafer is tested for fractional transmission at a plurality of points over its surface. A light beam from a suitable source such as a tungsten-halide lamp is passed through a monochromator and focused by a lens on the wafer. The fractional transmission (T) of light through the wafer is detected, amplified and fed to a computer where at least two points of transmission measurement are selected for calibration. One means of calibration is to compare the fractional transmission with at least two visually observed etch pit density points at identical locations. From these measurements, together with an estimate of the average etch pit size (area), the values for fractional transmission in regions of low etch pit density $T_O$ and high etch pit density $T_E$ may be calculated.

Having determined $T_O$ and $T_E$, the transmission data can be converted directly to etch pit density ($\rho_D$) according to the equation $$\rho_D = -\frac{1}{a} \ln \frac{T^{\frac{1}{2}} - T_E^{\frac{1}{2}}}{T_O^{\frac{1}{2}} - T_E^{\frac{1}{2}}}$$

By using this equation on all the measured transmission points, a total etch pit density map can be generated for the wafer under test.

Other features and advantages of the invention will be apparent from the following description, drawings and claims, which show and describe an embodiment of the invention.

DETAILED DESCRIPTION

The invention is an automated, digitized method and system for realizing dense, whole wafer etch pit maps of a GaAs surface. The invention is based on the fact that the etch pits scatter light strongly, and thus decrease the transmitted light. The situation is somewhat complicated at high etch pit densities because of overlapping pits, but an appropriate theory, which contains three parameters, can model this effect. One of the parameters is the average etch pit size, which can be measured with a calibrated microscope, while the other two parameters can be determined by visually or electronically counting the pits at two positions on the wafer. The pits can be electronically counted using a scanning electron microscope and electron scattering techniques. Even without this calibration, however, the degree of dislocation non-uniformity will be apparent in the transmission map itself.

Figure 1:
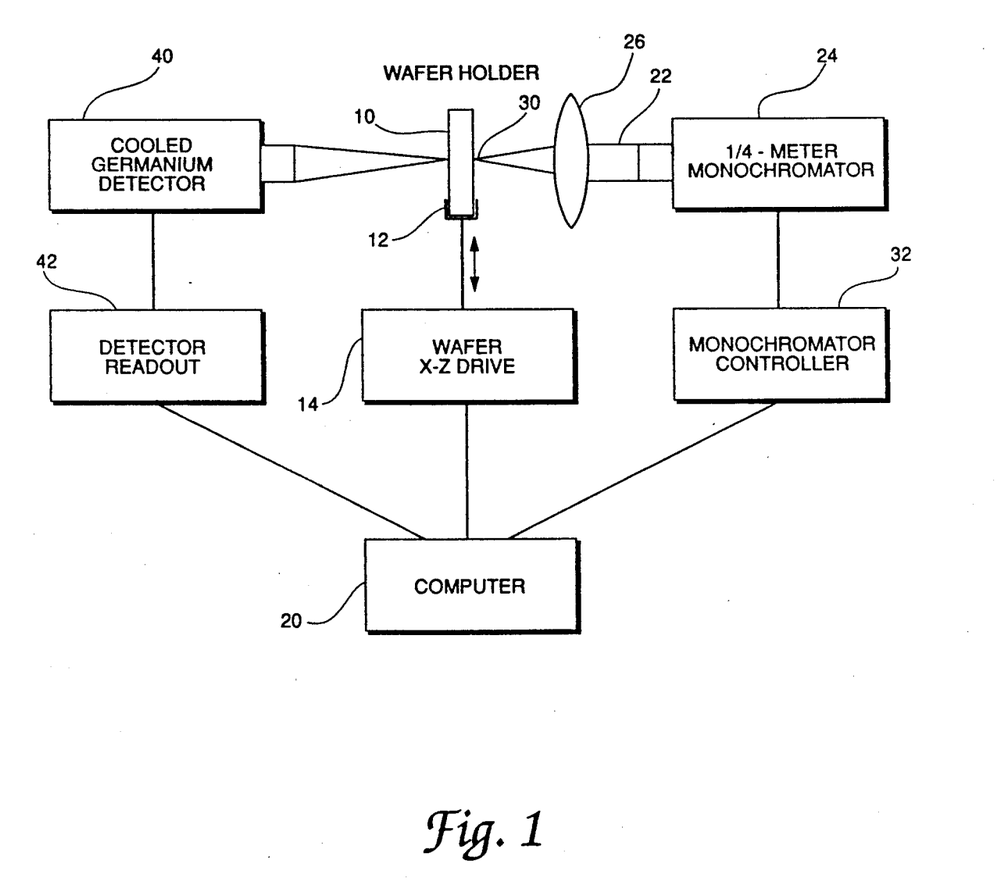
FIG. 1 is a block diagram of a system for achieving automated measurement of etch pit density in a GaAs wafer.

FIG. 1 shows a system according to the invention for achieving the automated etch pit density map. A GaAs wafer 10, for example, typically of 2–3 inches in diameter and 0.1 to 1.0 mm in thickness, is positioned in a wafer holder 12 attached to an X-Z drive apparatus 14 containing a Pair of electromechanical positioning mechanisms (not shown). The positioning mechanisms such as Newport 850-4 positioners manufactured by Newport Corporation, 18235 Mt. Baldy Circle, Fountain Valley Calif. 92728, are mounted at right angles in order to move the wafer holder 12 in two orthogonal directions. The "X" direction indicates a horizontal direction extending into and out of the view of FIG. 1, and the "Z" direction indicates a vertical direction. Positioning accuracy within 10 microns is achievable using a Newport model 855C positioning controller. The X-Z drive apparatus is controlled by a computer 20 to move wafer 10 in the path of an infrared light beam 22 generated by a ¼ meter monochromator 24. An optical lens 26 is used to focus the beam 22 into a small spot 30 of light on the surface of GaAs wafer 10. The ¼ monochromator 24 is a grating instrument which divides the light emitted by a suitable source such as a 50W tungsten-halogen lamp (not shown) into the single wavelength light beam 22. The intensity and wavelength of the light beam 22 are controlled by computer 20 through a monochromator controller 32 such as may be constructed from a SloSyn model M061-FF-411C3A stepper motor and Modulynx IOD010 motion controller, both manufactured by Superior Electric Co., 383 Middle Street, Bristol, Conn. 06010.

The fractional transmission of light spot 30 through the GaAs wafer 10 is measured by a cooled germanium detector 40 and coupled to a detector readout amplifier 42 for input to computer 20. The cooled germanium detector 40 is a 3 mm diameter planar p-n germanium junction mounted to a TO-5 header with an infrared transmitting window and a Peltier-junction cooler to reduce thermal noise. The combination of germanium doping materials, temperature, and window material can give a response that is linear with intensity over six decades of intensity.

To enhance the stability of the measurement, the infrared light beam 22 may be passed through a mechanical chopper before passing through the GaAs wafer 10 so that narrow-band synchronous amplification can be used. This also minimizes noise.

The relationship between transmission and etch pit density is complicated by the fact that the etch pits can overlap, especially if the pits are large and their density is high. The relationship can be expressed mathematically as follows. Let $A_T$ be the total illuminated-spot size, and let $A_E$ be the area within this spot size covered by etch pits. If dn etch pits of average area (a) are added, then the increase in $A_E$, i.e., $dA_E$, is $adn(1-A_E/A_T)$, to take account of the fact that some of the new etch pits will fall on areas already covered. If etch pit density is defined on a single surface as $\rho_D \equiv n/A_T$, the resulting differential equation yields $A_E/A_T = [1-\exp(-a\rho_D)]$.

The fraction of light scattered by area $A_E$ can be defined as $S \equiv \beta A_E/A_T = \beta[1-\exp(-a\rho_D)]$, where the parameter $\beta$ can range from 0 to 1, depending on the scattering strength of the etch pits. If $\beta=0$, then none of the light is scattered, whereas, if $\beta=1$, then all of it is scattered and assumed to miss the detector. Since two etched surfaces are involved, multiple scatterings and reflections must be considered. If S is the same for both surfaces (i.e., both sides etched) then it can be shown that the transmission T is given by $$T = \frac{(1-R)^2 (1-S)^2 e^{-ad}}{1 - R^2 (1-S)^2 e^{-2ad}} \quad (1)$$

where $\alpha$ is the absorption coefficient, d the wafer thickness, and R the reflectivity. In general, $R^2(1-S)^2 << 1$, and the wavelength is chosen such that $\alpha \approx 0$. By replacing the unknown parameters R and $\beta$ by more convenient parameters $T_O$ and $T_E$, where $T_O = T(a\rho_D << 1)$, and $T_E = T(a\rho_D >> 1)$, then Eq. 1 can be shown to yield $$T^{\frac{1}{2}} = T_E^{\frac{1}{2}} + (T_O^{\frac{1}{2}} - T_E^{\frac{1}{2}})e^{-a\rho_D} \quad (2)$$

For wafers which have both very high ($\rho_D a >> 1$) and very low ($\rho_D a << 1$) etch pit density regions, $T_O$ is simply the maximum, and $T_E$ the minimum measured transmission. However, in general, it is better to carry out an actual etch pit count at two points. Then, $T_O$ and $T_E$ can be related to the actual counts ($\rho_{D1}$ and $\rho_{D2}$) and the fractional transmissions ($T_1$ and $T_2$) at these two points can be expressed as $$T_O^{\frac{1}{2}} = \frac{T_2^{\frac{1}{2}}(1 - e^{-a\rho_{D1}}) - T_1^{\frac{1}{2}}(1 - e^{-a\rho_{D2}})}{e^{-a\rho_{D2}} - e^{-a\rho_{D1}}} \quad (3)$$

$$T_E^{\frac{1}{2}} = \frac{T_1^{\frac{1}{2}} e^{-a\rho_{D2}} - T_2^{\frac{1}{2}} e^{-a\rho_{D1}}}{e^{-a\rho_{D2}} - e^{-a\rho_{D1}}} \quad (4)$$

With these values of $T_O$ and $T_E$, the transmission data can be converted directly to etch pit data by inverting Eq. 2, such that $$\rho_D = -\frac{1}{a} \ln \frac{T^{\frac{1}{2}} - T_E^{\frac{1}{2}}}{T_O^{\frac{1}{2}} - T_E^{\frac{1}{2}}} \quad (5)$$

Figure 2:
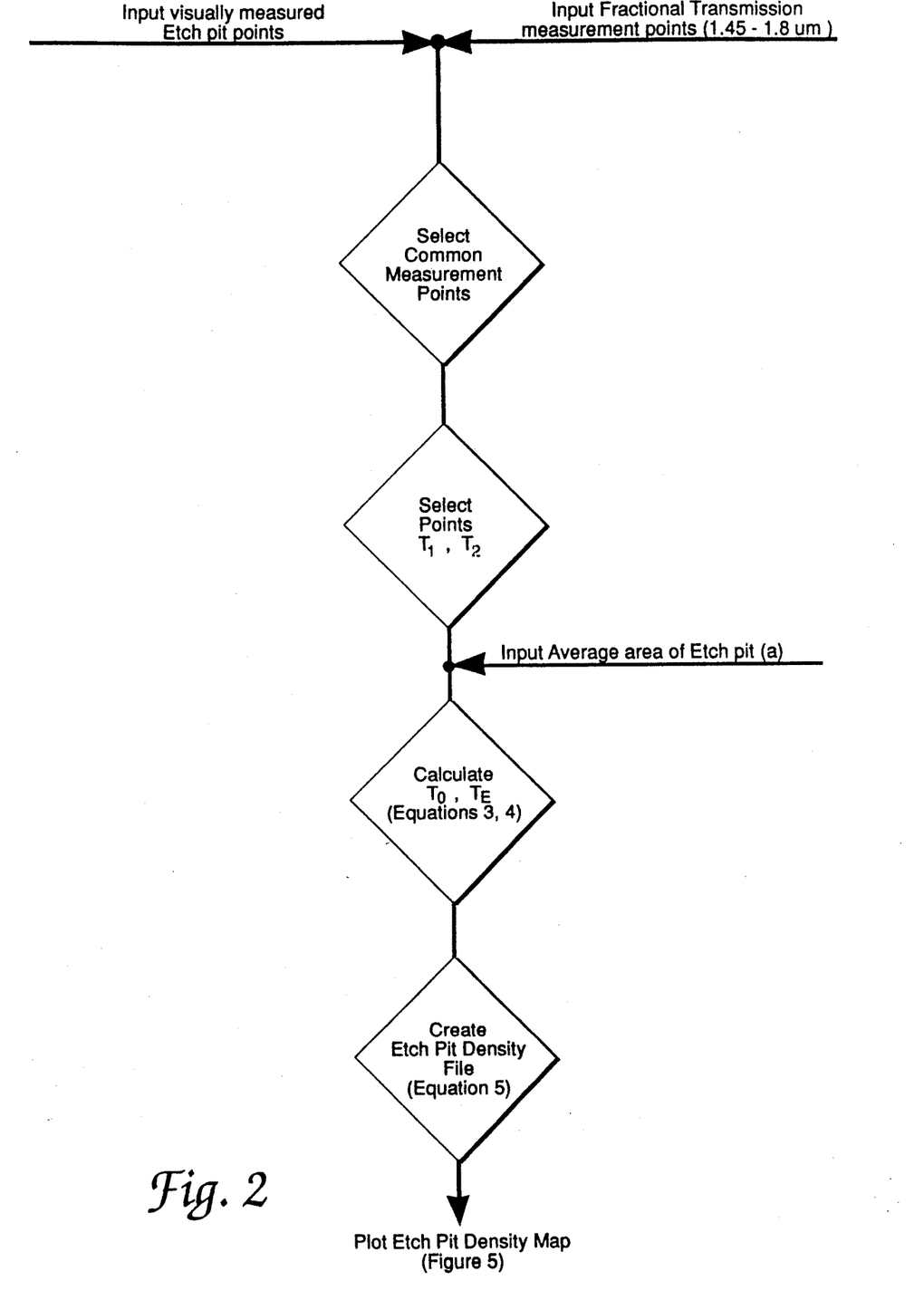
FIG. 2 is a flow diagram of the process for generating etch pit density maps according to the invention.

The invention may be illustrated by reference to the flow diagram of FIG. 2 in conjunction with the following example in which an etch pit map was generated from a GaAs low pressure liquid encapsulated-Czochralski wafer etched in molten KOH, at 450° C. for 40 minutes, in a zirconium crucible. Etch pits were visually counted at 166 locations, along horizontal [0$\bar{1}$1], vertical [0$\bar{1}\bar{1}$], and diagonal [0$\bar{1}$0] directions. The counting was carried out on 0.41×0.41 mm areas, centered on points 1 mm apart in the horizontal and vertical directions and 4.2 mm apart in the diagonal direction. The average etch pit size a was estimated, with a calibrated microscope to be $a=1.5\times10^{-5}$ cm². These data are summarized in FIG. 3, and show strong "W" patterns in the horizontal and vertical data slices.

After visually counting the etch pits, the wafer was mounted in the holder 12 shown in FIG. 1 and the transmission at 1.45 μm was measured at 3851 points on the wafer surface. The results are shown in FIG. 4, in which the horizontal and vertical slices are now "M" patterns rather than "W" patterns, because the transmission varies inversely with the etch pit density.

To calibrate the transmission data shown in FIG. 4, two points, $T_1$ and $T_2$, were calibrated against two visually counted etch pit density points, $\rho_{D1}$ and $\rho_{D2}$, at identical locations. In this particular case, more points were available for the calibration, since 166 points were visually counted. However, in general, it is necessary to obtain only two visual points to obtain the parameters $T_O$ and $T_E$. It is usually advantageous to read $T_O$ in a region of low etch pit density (high transmission) and $T_E$ in a region of high etch pit density (low transmission). If, further, the wafer has regions of very low etch pit density, such that $a\rho_{D1} \ll 1$, and regions of very high etch pit density, such that $a\rho_{D2} \gg 1$, then $T_O \approx T_1$, and $T_E \approx T_2$. In such a case, it is not necessary to visually count any points.

Figure 3:
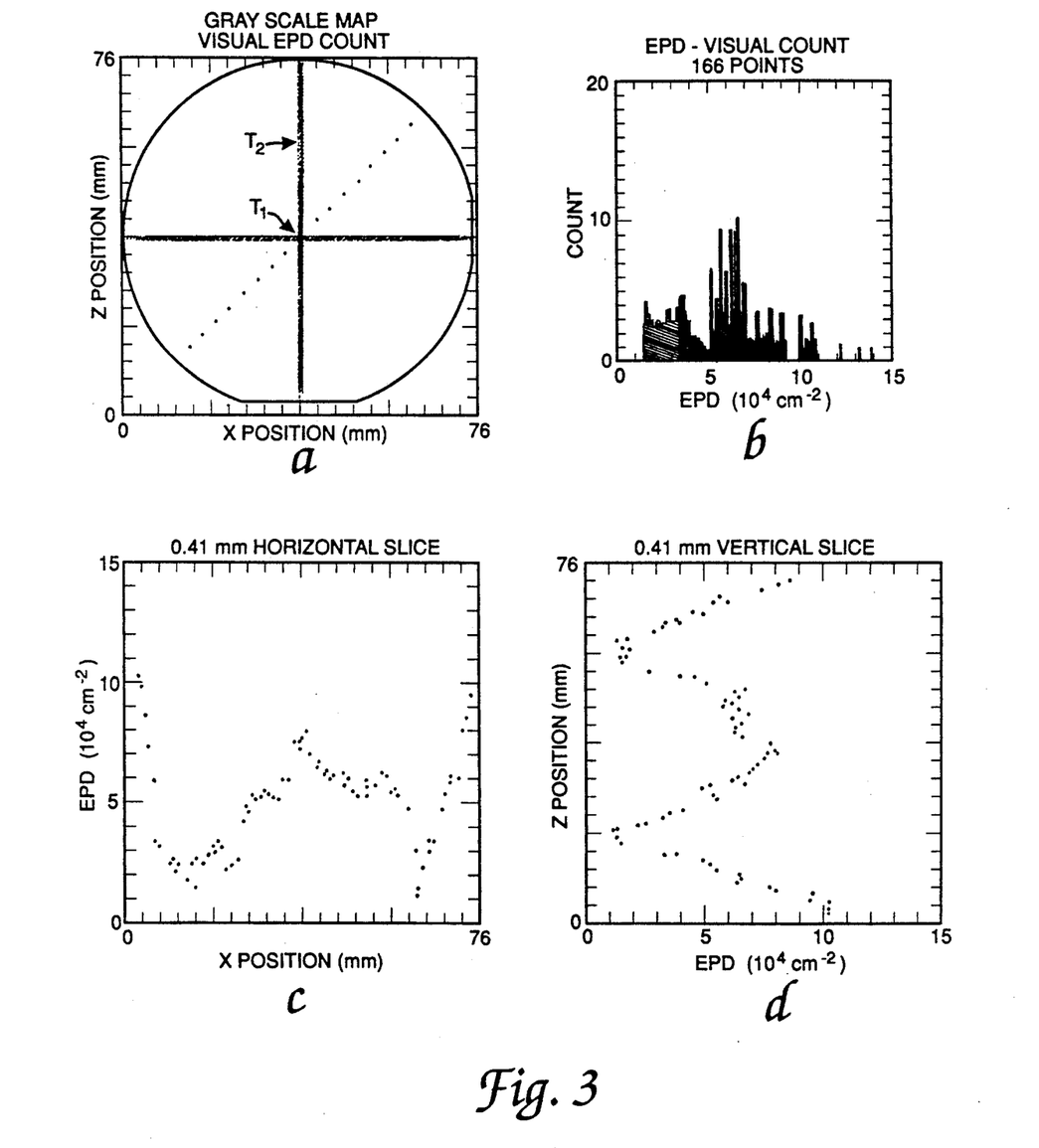
FIGS. 3a–d are a gray-scale map, a histogram, and horizontal and vertical slice patterns showing visually counted etch pit density in a low pressure liquid encapsulated-Czochralski (LEC) wafer.
Figure 4A:
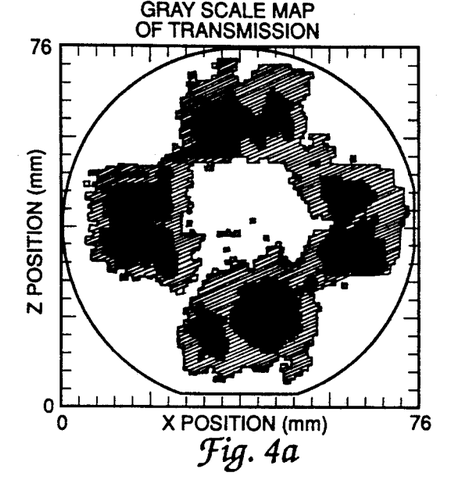
FIGS. 4a–d are a gray-scale map, a histogram, and horizontal and vertical slice patterns showing fractional transmission (T) at 1.45 μm in the LEC wafer.
Figure 4B:
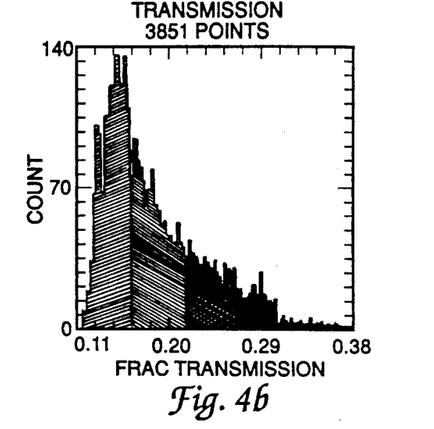
Figure 4C:
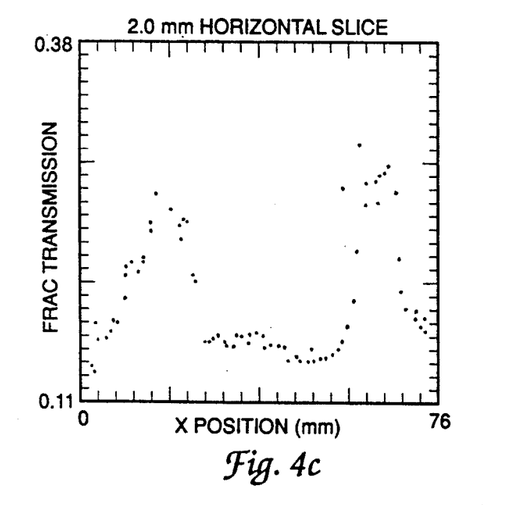
Figure 4D:
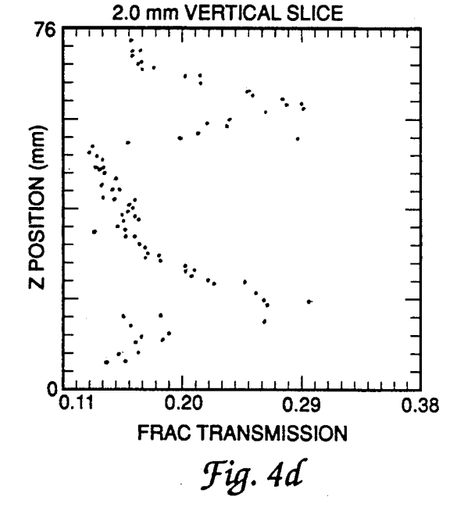
Figure 5:
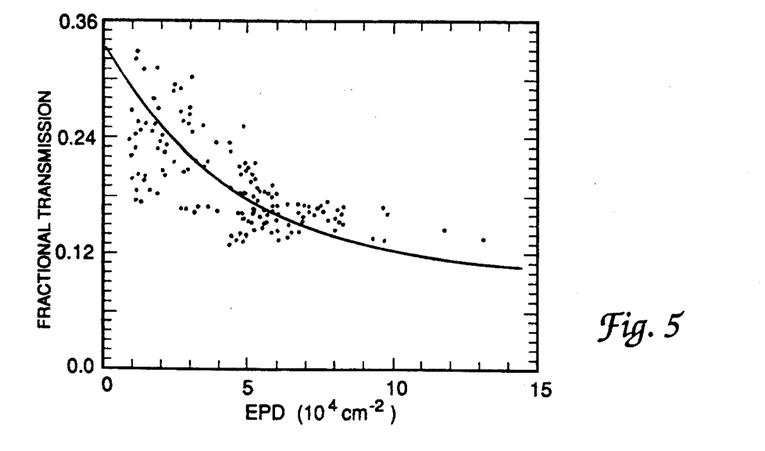
FIG. 5 is a graph showing fractional transmission (T) versus visually counted etch pit density at common points of measurement on the LEC wafer.
Figure 6A:
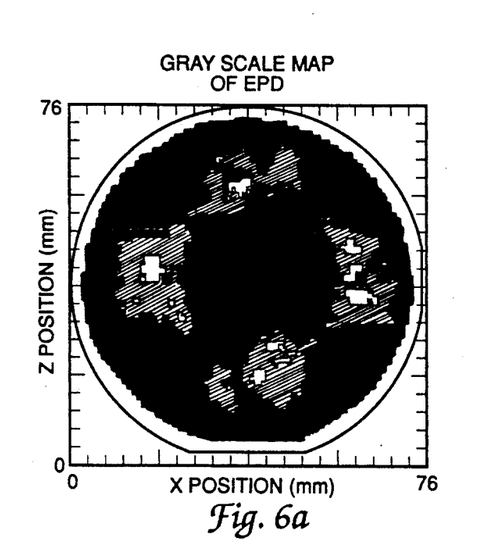
FIGS. 6a–d are a gray-scale map, a histogram and horizontal and vertical slice patterns showing a complete etch pit density map for the LEC wafer as determined by the method and system of the invention.
Figure 6B:
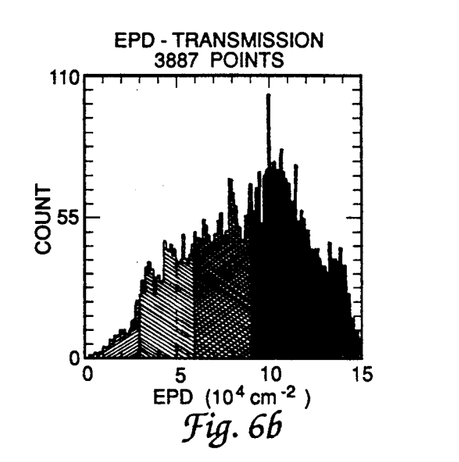
Figure 6C:
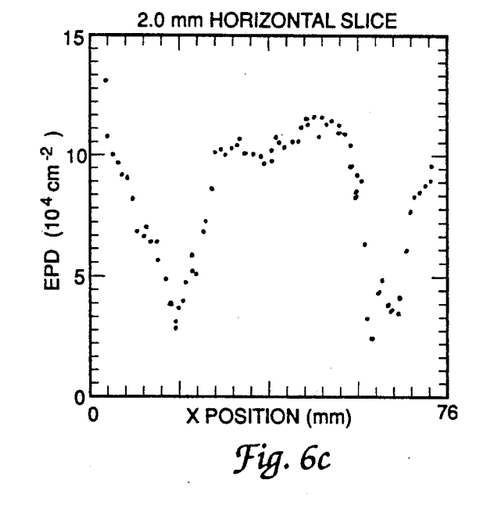
Figure 6D:
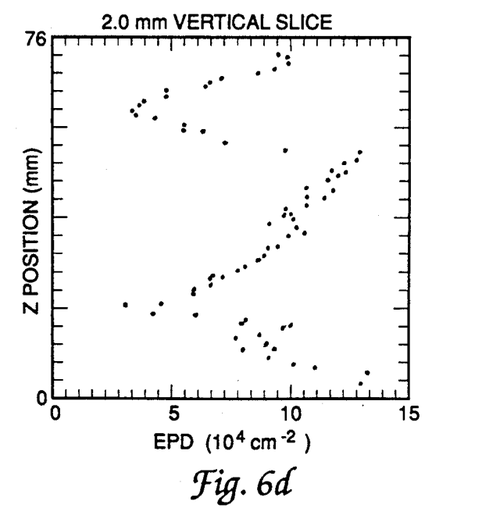

For this example the two counting locations shown in FIG. 3 were chosen and thus determined $T_O$ and $T_E$. Since the average etch pit size a was already determined, Eq. 2 can be plotted, and is shown as the solid line in FIG. 5. Also represented are the 166 visually counted points, and it is seen that they scatter evenly about the theoretical relationship. Thus, Eq. 2 is validated as a calibration curve, and is used in inverted form (Eq. 5) to obtain the complete etch pit map from the transmission map, as shown in FIG. 6. A program listing for the software used in computer 20 to generate the etch pit density map of FIG. 6 is incorporated herein as Appendix A.

Thus, while preferred features of the invention are described and illustrated herein, it is understood that changes and variations may be made by those skilled in the art without departing from the spirit and scope of the invention.

APPENDIX A

```
SUBROUTINE CORMENU(ISET,ISET1,ISET2,CORAY,NPAIRS,CLIPMIN,
1CLIPMAX,INC,TXT,IXTICS,IXBIGTICS,CXFMT,ISAVE,ICOLX,ICOLY,
1XSIZE,YSIZE,NXFMT,XPOS,YPOS,DATA,DATANAME,NPTS,IGIN,IAXISX,
1IAXISY,ICLRS,IDIAMETER,TITLE1)

REAL CORAY(40000,7),CLIPMIN(10),CLIPMAX(10),XPOS(10,40000)
  REAL YPOS(10,40000),DATA(10,40000),AAA(30)
  REAL AVG(10),STDEV(10),MEDIAN(10),LOWQUART(10)
  REAL UPQUART(10),REGMIN,REGMAX,AMP(6),DAMP(6),ERATE(6)
  REAL COFF,DCOFF,DERATE(6),XVALUE

INTEGER ISET,ISET1,ISET2,NPAIRS,IFUN,ILINDEX,INC
  INTEGER NPTS(10),NXFMT(10),IXTICS(10),IXBIGTICS(10),JX(100)
  INTEGER JY(100)

CHARACTER*50 CAR1(60),CAR(60),TXT(60,20),TITLE,TITLE1(10)
  CHARACTER*14 DATANAME(10),EPDFILE
  CHARACTER*35 PROMPT
  CHARACTER*10 SLOPEV,YINTV,OFFSETCHAR
  CHARACTER*10 CERATE,CDERATE,CTO,CDTO,CTE,CDTE
  CHARACTER*15 CXFMT(10)
  CHARACTER*1 DUMMY,CHOICE

DIMENSION REGTOT(100),REGNUM(100),REGAVG(100)
  DIMENSION REGARRAY(40000,7),XMID(100),TRANS(1000),EPD(1000)

XSCALE(X)=(X-CLIPMIN(ISET1))*10000/(CLIPMAX(ISET1)-CLIPMIN
 1(ISET1))
  YSCALE(Y)=(Y-CLIPMIN(ISET2))*10000/(CLIPMAX(ISET2)-CLIPMIN
 1(ISET2))

ILSEG=10000+(ISET-1)*200+90      !STARTING SEGMENT FOR FITTED LINES

ISET10=ISET+10                   !ISET10 USED IN TEXT ARGUMENTS

PROMPT = '                       CHOICE: '
  CALL LLSLVW(40+ISET*3-1)
  CALL CURSOR
  CALL LLDACL
  CALL LLDUMP

CAR(24)='('''$(A)                     LINE COLOR: '')'
  CAR(25)='('''$(B)              LINE STYLE (0-7): '')'
  CAR(26)='('''$(C)                       FUNCTION: '')'
  CAR1(24)='('''   (A)                  LINE COLOR: '',I3)'
  CAR1(25)='('''   (B)           LINE STYLE (0-7): '',I3)'
  CAR1(26)='('''   (C)                    FUNCTION: '',I3)'
```

```
CAR1(27)='('' (D)         PLOT FUNCTION: '')'
CAR1(28)='('' (E)    ANALYZE TRANS/EPD DATA: '')'
CAR1(29)='('' (F)CHANGE COLOR ON SCATTER MAP: '')'
CAR1(30)='('' (G)   CHANGE COLOR ON WAFER MAP: '')'
CAR1(31)='('' (H)    FIT LINE TO SET OF POINTS: '')'
CAR1(32)='('' (I)         SUBSET CORRELATION: '')'
CAR1(34)='('' (J)                  TEXT MENU: '')'
CAR1(35)='('' (K)                  AXES MENU: '')'
CAR1(36)='('' (L)         RE-CORRELATE & PLOT: '')'
CAR1(37)='('' (M)               RE-PLOT AXES: '')'
CAR1(38)='('' (N)         ENTER TARGET RANGES: '')'
CAR1(33)='('' (Z)                       EXIT: '')'
LINEST=0
ILINDEX=4
IFUN=1
CALL LLLNIN(ILINDEX)
CALL LLDACL
CALL LLDUMP
WRITE(*,CAR1(24))ILINDEX
WRITE(*,CAR1(25))LINEST
WRITE(*,CAR1(26))IFUN
WRITE(*,CAR1(27))
WRITE(*,CAR1(28))
WRITE(*,CAR1(29))
WRITE(*,CAR1(30))
WRITE(*,CAR1(31))
WRITE(*,CAR1(32))
WRITE(*,CAR1(34))
WRITE(*,CAR1(35))
WRITE(*,CAR1(36))
WRITE(*,CAR1(37))
WRITE(*,CAR1(38))
WRITE(*,CAR1(33))

CALL QUERY(PROMPT,CHOICE)
CALL LLDUMP
IF (CHOICE.EQ.'A') THEN
   WRITE(*,CAR(24))
   READ(*,*)ILINDEX
   CALL LLLNIN(ILINDEX)
ELSEIF (CHOICE.EQ.'B') THEN
   WRITE(*,CAR(25))
   READ(*,*)LINEST
   CALL LLLNST(LINEST)
ELSEIF (CHOICE.EQ.'C') THEN
   WRITE(*,CAR(26))
   READ(*,*)IFUN
ELSEIF (CHOICE.EQ.'D') THEN
   CALL PLOTFUN(ISET,IFUN,CLIPMIN,CLIPMAX,ISET1,ISET2,0.0,0.0,0.0,
1 NN,AAA)
ELSEIF (CHOICE.EQ.'E') THEN
     CALL LLDLSG(10000+(ISET-1)*200+50+8)    !DELETE PREV BINNED PTS
     CALL LLDLSG(10000+(ISET-1)*200+180+9)   !DELETE PREV LINE
   CALL LLSLVW(40+ISET*3)
   WRITE(*,('' THIS OPTION IS USED TO CALIBRATE EPD DATA '')')
   WRITE(*,(''$     EXIT(0) OR CONTINUE(1): '')')
   READ*,ICONTINUE
   IF (ICONTINUE.EQ.0) GOTO 25
   WRITE(*,(''$     BINS(0) OR ACTUAL DATA(1): '')')
   READ*,JCH
   IF (JCH.EQ.0) THEN
     ILINDEX=4
     IMARSEG=10000+(ISET-1)*200+50+ILINDEX       !BINNED POINTS
     CALL LLDLSG(10000+(ISET-1)*200+110+INC)
     CALL LLOPSG(10000+(ISET-1)*200+110+INC)
     WRITE(*,(''$     ENTER NUMBER OF REGIONS: '')')
     READ*,IREGIONS
     ITOTPOINTS=0
     DO 40 I=1,IREGIONS
```

```
         REGMIN=CLIPMIN(ISET1)+(I-1)*(CLIPMAX(ISET1)-CLIPMIN(ISET1))/
1        IREGIONS
         REGMAX=CLIPMIN(ISET1)+(I)*(CLIPMAX(ISET1)-CLIPMIN(ISET1))/
1        IREGIONS
         REGNUM(I)=0
         REGTOT(I)=0
         DO 50 J=1,NPAIRS
            IF (CORAY(J,1).GE.REGMIN.AND.CORAY(J,1).LT.REGMAX) THEN
               REGNUM(I)=REGNUM(I)+1
               REGTOT(I)=REGTOT(I)+CORAY(J,2)
            END IF
         CONTINUE
         IF (REGNUM(I).EQ.0) GOTO 40
         ITOTPOINTS=ITOTPOINTS+1
         REGAVG(I)=REGTOT(I)/REGNUM(I)
         XMID(I)=(REGMAX-REGMIN)/2.0+REGMIN
         REGARRAY(ITOTPOINTS,1)=XMID(I)
         REGARRAY(ITOTPOINTS,2)=REGAVG(I)
         JX(I)=XSCALE(REGARRAY(ITOTPOINTS,1))
         JY(I)=YSCALE(REGARRAY(ITOTPOINTS,2))
         REGARRAY(ITOTPOINTS,5)=4
         CALL LLCAS4(IMARSEG,JX(I),JY(I),1)
      CONTINUE
      CALL LLCLSG
      CALL LLRNVW(40+ISET*3)
      CALL LLLNIN(ILINDEX)
      ILINDEX=8
      CALL CORBOX(ISET,REGARRAY,ITOTPOINTS,ILINDEX,INC,IFLG,
1     CLIPMIN,CLIPMAX,ISET1,ISET2,1,IGIN,IDIAMETER)
   ELSE
      ILINDEX=8
      CALL LLLNIN(ILINDEX)
      CALL CORBOX(ISET,CORAY,NPAIRS,ILINDEX,INC,IFLG,CLIPMIN,
1     CLIPMAX,ISET1,ISET2,1,IGIN,IDIAMETER)
   END IF
   CALL LLDUMP
   WRITE(*,'(''$    ENTER AVG ETCH PIT SIZE (cm^2): '')')
   READ*,SLOPE
   IF (JCH.EQ.0) THEN
      CALL LOGGER(ISET,ITOTPOINTS,REGARRAY,OFFSET,SLOPE,YINT,TXT,
1     ILSEG,ISET10,CLIPMIN,CLIPMAX,ISET1,ISET2)
   ELSE
      CALL LOGGER(ISET,NPAIRS,CORAY,OFFSET,SLOPE,YINT,TXT,
1     ILSEG,ISET10,CLIPMIN,CLIPMAX,ISET1,ISET2)
   END IF
   IF (YINT.LE.OFFSET) THEN
      WRITE(*,*)'A=',SLOPE,'T0=',YINT,'TE=',OFFSET
      WRITE(*,*)'ETCH PIT SIZE IS TOO SMALL.  TRY AGAIN'
      GOTO 52
   END IF
   CALL LLLNIN(8)
   CALL LLDUMP
   CALL PLOTFUN(ISET,9,CLIPMIN,CLIPMAX,ISET1,ISET2,SLOPE,
1  YINT,OFFSET,NN,AAA)
   ERATE(1)=SLOPE
   AMP(1)=YINT**0.5-OFFSET**0.5
   COFF=OFFSET**0.5
   WRITE(*,'(''$    CREATE AN EPD FILE NO(0) YES(1): '')')
   READ*,IEPD
   IF (IEPD.EQ.1) THEN
      WRITE(*,'(''$         ENTER NEW EPD FILE NAME: '')')
      READ(*,'(A14)')EPDFILE
      OPEN(UNIT=10,STATUS='NEW',FILE=EPDFILE,ERR=61)
      DO 60 I=1,NPTS(ISET2)
         IF (DATA(ISET2,I).LT.0) DATA(ISET2,I)=0.0
         XVALUE=(DATA(ISET2,I)**0.5-OFFSET**0.5)/
1        (YINT**0.5-OFFSET**0.5)
         IF (XVALUE.LE.0.0) THEN
            EPDDATA=1E+30
         ELSE
```

```
             EPDDATA=LOG(XVALUE)/SLOPE*-1.0
           END IF
           WRITE(10,*,ERR=60)XPOS(ISET2,I),YPOS(ISET2,I),EPDDATA
         CONTINUE
         CLOSE(10)
       END IF
       CALL EPDCONVERT(DATA,XPOS,YPOS,EPDFILE,ISET2,NPTS)
         WRITE(*,'(''$  ENTER (0) TO CONTINUE (1) TO FIT EXPONENTIAL
      1: '')')
         READ*,IEXP
         IF (IEXP.EQ.1) THEN
           OPEN(UNIT=3,FILE='WAFEX.DAT',STATUS='NEW')
      1    IAXISY,CXFMT(ISET1),NXFMT(ISET1),CXFMT(ISET2),NXFMT(ISET2),
      1    IOMITX,IOMITY,TITLE1(ISET1),TITLE1(ISET2),TITLE,ICHN)
       ELSEIF (CHOICE.EQ.'L') THEN
           CALL CORRELATE(ISET,XPOS,YPOS,DATA,DATANAME,NPTS,AVG,STDEV,
      1    CLIPMIN,CLIPMAX,CXFMT,NXFMT,IXTICS,IXBIGTICS,MEDIAN,LOWQUART,
      1    UPQUART,ISET1,ISET2,TXT,TITLE1,1,IGIN,IAXISX,IAXISY,ICLRS,
      1    IDIAMETER)
       ELSEIF (CHOICE.EQ.'M') THEN
           CALL LLDUMP
           CALL LLSLVW(40+ISET*3-1)
           CALL LLDLSG(10000+(ISET-1)*200+102)
           CALL LLDLSG(10000+(ISET-1)*200+101)
           CALL LLOPSG(10000+(ISET-1)*200+101)
           CALL PDATE(10000)
           TITLE=DATANAME(ISET2)//' vs '//DATANAME(ISET1)
           CALL AXES(CLIPMIN(ISET1),CLIPMAX(ISET1),CLIPMIN(ISET2),
      1    CLIPMAX(ISET2),IXBIGTICS(ISET1),IXBIGTICS(ISET2),
      1    IXTICS(ISET1),IXTICS(ISET2),IXGRID,IYGRID,IGLINST,IAXISX,
      1    IAXISY,CXFMT(ISET1),NXFMT(ISET1),CXFMT(ISET2),NXFMT(ISET2),
      1    IOMITX,IOMITY,TITLE1(ISET1),TITLE1(ISET2),TITLE,1)
           CALL LLCLSG
           CALL LLSLVW(40+ISET*3)
           CALL LLRNVW(0)
       ELSEIF (CHOICE.EQ.'N') THEN
           CALL TARGET(ISET,CLIPMIN,CLIPMAX,ISET1,ISET2,CORAY,ILINDEX,
      1    NPAIRS,INC,IDIAMETER)
           CALL LLDUMP
           CALL LLSLVW(40+ISET*3-1)
           CALL LLDLSG(10000+(ISET-1)*200+102)
           CALL LLDLSG(10000+(ISET-1)*200+101)
           CALL LLOPSG(10000+(ISET-1)*200+101)
           CALL PDATE(10000)
           TITLE=DATANAME(ISET2)//' vs '//DATANAME(ISET1)
           CALL AXES(CLIPMIN(ISET1),CLIPMAX(ISET1),CLIPMIN(ISET2),
      1    CLIPMAX(ISET2),IXBIGTICS(ISET1),IXBIGTICS(ISET2),
      1    IXTICS(ISET1),IXTICS(ISET2),0,0,0,IAXISX,
      1    IAXISY,CXFMT(ISET1),NXFMT(ISET1),CXFMT(ISET2),NXFMT(ISET2),
      1    0,0,TITLE1(ISET1),TITLE1(ISET2),TITLE,1)
           CALL LLCLSG
       ELSEIF (CHOICE.EQ.'Z') THEN
           GOTO 30
       ELSE
           GOTO 20
       ENDIF
       CALL LLDACL
       CALL LLDUMP
       GOTO 20
       RETURN
       END
```

---

```
      SUBROUTINE TARGET(ISET,CLIPMIN,CLIPMAX,ISET1,ISET2,CORAY,ILINDEX,
     1NPAIRS,INC,IDIAMETER)

REAL CLIPMIN(10),CLIPMAX(10),XTARGMIN,XTARGMAX,YTARGMIN,YTARGMAX
      REAL CORAY(40000,7)
```

```
      INTEGER ISET,ISET1,ISET2,IXLL1,IXUR1,IYLL1,IYUR1,IXLL2,IXUR2
      INTEGER IYLL2,IYUR2,INC,LINDEX,NPAIRS,ISAVE(20000),ISC,ICOL
      INTEGER NCHANGE

XSCALE(X)=INT(10000*(X-CLIPMIN(ISET1))/(CLIPMAX(ISET1)-CLIPMIN
     1(ISET1)))
      YSCALE(Y)=INT(10000*(Y-CLIPMIN(ISET2))/(CLIPMAX(ISET2)-CLIPMIN
     1(ISET2)))
      XREAL(Z)=(Z+RAD)*10000/DIAM
      DIAM=IDIAMETER*25.4
      RAD=DIAM/2

CALL LLDUMP
      INC=INC+1
      WRITE(*,'(''$ ENTER X TARGET RANGE (MIN,MAX): '')')
      READ*,XTARGMIN,XTARGMAX
      WRITE(*,'(''$ ENTER Y TARGET RANGE (MIN,MAX): '')')
      READ*,YTARGMIN,YTARGMAX
      IXLL1=XSCALE(XTARGMIN)
      IXUR1=XSCALE(XTARGMAX)
      IYLL2=YSCALE(YTARGMIN)
      IYUR2=YSCALE(YTARGMAX)
      CALL LLSLVW(40+(ISET*3))
      CALL LLDLSG(10000+200*(ISET-1)+190)
      CALL LLOPSG(10000+200*(ISET-1)+190)
      CALL LLLNIN(6)
      CALL LLSFIL(-6)
      CALL LLMOV4(IXLL1,0)
      CALL LLBPN4(IXLL1,0,1)
      CALL LLDRA4(IXUR1,0)
      CALL LLDRA4(IXUR1,IYLL2)
      CALL LLDRA4(10000,IYLL2)
      CALL LLDRA4(10000,IYUR2)
      CALL LLDRA4(IXUR1,IYUR2)
      CALL LLDRA4(IXUR1,10000)
      CALL LLDRA4(IXLL1,10000)
      CALL LLDRA4(IXLL1,IYUR2)
      CALL LLDRA4(0,IYUR2)
      CALL LLDRA4(0,IYLL2)
      CALL LLDRA4(IXLL1,IYLL2)
      CALL LLDRA4(IXLL1,0)
      CALL LLEPNL
      CALL LLLNIN(1)
      CALL LLMOV4(IXLL1,0)
      CALL LLDRA4(IXLL1,10000)
      CALL LLMOV4(IXUR1,0)
      CALL LLDRA4(IXUR1,10000)
      CALL LLMOV4(0,IYLL2)
      CALL LLDRA4(10000,IYLL2)
      CALL LLMOV4(0,IYUR2)
      CALL LLDRA4(10000,IYUR2)
      CALL LLCLSG
      ILINDEX=8
      CALL LLLNIN(8)
      CALL LLSFIL(-8)
      ISC=0
      DO 25 I=1,INC
         CALL LLDLSG(10000+(ISET-1)*200+110+I)
      CONTINUE
      CALL LLOPSG(10000+(ISET-1)*200+110+INC)
      DO 30 I=1,NPAIRS
         IF (CORAY(I,1).GE.XTARGMIN.AND.CORAY(I,1).LE.XTARGMAX.AND.
     1   CORAY(I,2).GE.YTARGMIN.AND.CORAY(I,2).LE.YTARGMAX) THEN
            ISC=ISC+1
            ISAVE(ISC)=I
            CORAY(I,5)=ILINDEX
            IX=XSCALE(CORAY(I,1))
            IY=YSCALE(CORAY(I,2))
            MSEG=(10000+(ISET-1)*200+50+ILINDEX)
```

```fortran
        CALL LLCAS4(MSEG,IX,IY,2)      ! CALL THE CURRENT MARKER
     NCHANGE=NCHANGE+1
  ELSE
     IX=XSCALE(CORAY(I,1))
     IY=YSCALE(CORAY(I,2))
        CORAY(I,5)=4
        MSEG=(10000+(ISET-1)*200+50+CORAY(I,5))
        CALL LLCAS4(MSEG,IX,IY,2)
     END IF
  CONTINUE
  CALL LLCLSG
  CALL LLRNVW(0)
  CALL LLSLVW(40+ISET*3-2)
  CALL LLDLSG(10000+(ISET-1)*200+140+INC)
  CALL LLOPSG(10000+(ISET-1)*200+140+INC)
  DO 40 I=1,NCHANGE
     IX=XREAL(CORAY(ISAVE(I),3))
     IY=XREAL(CORAY(ISAVE(I),4))
     ICOL=(10000+(ISET-1)*200+ILINDEX-1)       ! IN SQUARE, K=K+1
     CALL LLCAS4(ICOL,IX,IY,1)         ! CALLING A PREMADE SQUARE
  CONTINUE
  CALL LLCLSG
  CALL LLDUMP
  RETURN
  END

----------------------------------------------------------------

SUBROUTINE BDEFINE(IXLL,IYLL,IXUR,IYUR,IGIN)

DIMENSION XDEF(0:100)

CHARACTER*50 CAR(2)
  CHARACTER*1 KEYCHR,SIGCHAR

IF (IGIN.EQ.8) THEN
     IGD=64
  ELSE
     IGD=0
  END IF
  CALL LLDACL
  CALL LLDUMP
  CALL LLCRGN(IGD,3)    ! THUMBWHEELS LOCATE; SEGMENT 3.
  CALL LLENGN(IGD,20)   ! THUMBWHEELS LOCATE; 20 MAX. EVENTS.
  CALL LLGTG4(SIGCHAR,KEYCHR,IXLL,IYLL,JS,JP)
  CALL LLGTG4(SIGCHAR,KEYCHR,IXUR,IYUR,JS,JP)
  CALL LLDSGN(IGD)      ! DISABLE THUMBWHEELS LOCATE.

GET FINAL REPORT

CALL LLGTG4(SIGCHAR,KEYCHR,IX,IY,JS,JP)
  CALL LLDACL
  CALL LLDUMP
  RETURN
  END

SUBROUTINE LOGGER(ISET,NPAIRS,CORAY,OFFSET,SLOPE,YINT,TXT,ILSEG,
 1ISET10,CLIPMIN,CLIPMAX,ISET1,ISET2)

REAL CORAY(40000,7),CORAY1(40000,7),OFFSET,SLOPE,YINT,TEMP
  REAL CLIPMIN(10),CLIPMAX(10)

INTEGER ISET,NPAIRS,NPAIRS1,ICOL

CHARACTER*50 TXT(60,20)
  CHARACTER*10 OFFSETCHAR,SLOPEV,YINTV
  CHARACTER*25 CONFILE

SLOPE=ABS(SLOPE)
  WRITE(*,'(''S ENTER COLOR OF POINTS FOR FIT: '')')
```

```
       READ(*,*) ICOL
       ICOL=8
       NPAIRS1=0
       DO 10 I=1,NPAIRS
         IF (CORAY(I,5).EQ.ICOL) THEN
           NPAIRS1=NPAIRS1+1
           CORAY1(NPAIRS1,2)=CORAY(I,2)
           CORAY1(NPAIRS1,1)=CORAY(I,1)
         END IF
       CONTINUE
       IF (NPAIRS1.EQ.2) THEN
         CALL FIT3(CORAY1,TA,TB,SLOPE)
         OFFSET=TB
         YINT=TA
       ELSE
         WRITE(*,'('' TOO MANY POINTS PICKED '')')
         RETURN
       END IF
       DO 15 I=1,NPAIRS1
         TEMP=CORAY1(I,2)-TB
         IF (TEMP.GT.0) THEN
           CORAY1(I,2)=ABS(LOG(TEMP))
         END IF
       CONTINUE
        WRITE(*,'(''$  CREATE CONVERSION FILE (0)NO (1)YES: '')')
        READ(*,*)ICON
        IF (ICON.EQ.1) THEN
          WRITE(*,'(''$                              ENTER FILENAME: '')')
          READ(*,'(A25)') CONFILE
          CONFILE='[SEWELL.WCDA.EPD]'//CONFILE
          OPEN(UNIT=10,STATUS='NEW',FILE=CONFILE,ERR=20)
          WRITE(10,*) SLOPE,OFFSET,YINT
        END IF
       WRITE(OFFSETCHAR,'(1PE10.3)') OFFSET
       WRITE(SLOPEV,'(1PE10.3)') SLOPE
       WRITE(YINTV,'(1PE10.3)') YINT
       TXT(54,ISET10)='Te = '//OFFSETCHAR
       TXT(55,ISET10)='To = '//YINTV
       TXT(56,ISET10)='A = '//SLOPEV
       TXT(57,ISET10)='T = (Te**0.5+(To**0.5-Te**0.5)**-AX)**2.0'
       TXT(58,ISET10)='T = Transmission'
       TXT(59,ISET10)='X = EPD Count'
       TXT(60,ISET10)='A = Average Etch Pit Size'
       RETURN
       END

SUBROUTINE FIT3(CORAY1,TO,TE,A)

REAL TO,TE,CORAY1(40000,7),A,AA,BB,T1,T2,R1,R2

T1=CORAY1(1,2)       !TRANSMISSION 1
       T2=CORAY1(2,2)
       R1=CORAY1(1,1)       !ETCH PIT DENSITY 1
       R2=CORAY1(2,1)
       TO=(((T2**0.5)*(1-EXP(-1*A*R1))-(T1**0.5)*(1-EXP(-1*A*R2)))/
      1(EXP(-1*A*R2)-EXP(-1*A*R1)))**2.0
       TE=(((T1**0.5)*(EXP(-1*A*R2))-(T2**0.5)*(EXP(-1*A*R1)))/
      1(EXP(-1*A*R2)-EXP(-1*A*R1)))**2.0
       RETURN
       END

SUBROUTINE PLOTFUN(ISET,IFUN,CLIPMIN,CLIPMAX,ISET1,ISET2,
      .SLOPE,YINT,OFFSET,NN,AAA)

REAL CLIPMIN(10),CLIPMAX(10),DX,SLOPE,YINT,OFFSET,AAA(30)
       INTEGER IFUN,ISET,ISET1,ISET2,IFUNSEG

XSCALE(X)=(X-CLIPMIN(ISET1))*10000/(CLIPMAX(ISET1)-CLIPMIN(ISET1))
       YSCALE(Y)=(Y-CLIPMIN(ISET2))*10000/(CLIPMAX(ISET2)-CLIPMIN(ISET2))
```

```
      CALL LLSLVW(40+ISET*3)
      CALL LLRNVW(0)
      CALL LLDUMP
      IFUNSEG=10000+(ISET-1)*200+180+IFUN
      CALL LLDLSG(IFUNSEG)
      CALL LLOPSG(IFUNSEG)
      DX=(CLIPMAX(ISET1)-CLIPMIN(ISET1))/300
      I=0
      DO 400 X=CLIPMIN(ISET1),CLIPMAX(ISET1),DX
        XF=X
        IF (IFUN.EQ.1) Y=F1(XF,NN,AAA)
        IF (IFUN.EQ.2) Y=F2(XF)
        IF (IFUN.EQ.3) Y=F3(XF)
        IF (IFUN.EQ.4) Y=F4(XF)
        IF (IFUN.EQ.5) Y=F5(XF)
        IF (IFUN.EQ.6) Y=F6(XF)
        IF (IFUN.EQ.7) Y=F7(XF)
        IF (IFUN.EQ.8) Y=F8(XF)
        IF (IFUN.EQ.9) Y=F9(XF,SLOPE,YINT,OFFSET)
        CALL LLDUMP
        IX=XSCALE(X)
        IY=YSCALE(Y)
        IF (I.EQ.0) THEN
           CALL LLMOV4(IX,IY)
           I=1
        ELSE
           CALL LLDRA4(IX,IY)
        END IF
        CALL LLDUMP
      CONTINUE
      CALL LLCLSG
      RETURN
      END

FUNCTION F1(X,NN,AAA)
      DIMENSION AAA(30)
      F1=AAA(1)
      DO 10 I=2,NN+1
        F1=F1+(X**(I-1))*AAA(I)
      CONTINUE
      RETURN
      END

FUNCTION F2(X)
      F2=0.0
      RETURN
      END

FUNCTION F3(X)
      F3=0.0
      RETURN
      END

FUNCTION F4(X)
      F4=0.0
      RETURN
      END

FUNCTION F5(X)
      F5=0.0
      RETURN
      END

FUNCTION F6(X)
      F6=0.0
      RETURN
      END
```

```
FUNCTION F7(X)
F7=0.0
RETURN
END

FUNCTION F8(X)
F8=0.0
RETURN
END

FUNCTION F9(X,A,TO,TE)
F9=(TE**0.5+(TO**0.5-TE**0.5)*EXP(-1*A*X))**2.0
RETURN
END
      WRITE(3,*)IREGIONS,2
        IF (JCH.EQ.0) THEN                        !BINS
          DO 290 I=1,ITOTPOINTS
            TRANS(I)=REGARRAY(I,2)**0.5
            EPD(I)=REGARRAY(I,1)
            WRITE(3,*)EPD(I),TRANS(I)
          CONTINUE
          WRITE(3,*)ERATE(1),AMP(1),COFF
          CLOSE(3)
          NMP=ITOTPOINTS
        ELSE IF (JCH.EQ.1) THEN                   !ALL DATA
          DO 300 I=1,NPAIRS
            TRANS(I)=CORAY(I,2)**0.5
            EPD(I)=CORAY(I,1)
          CONTINUE
          NMP=NPAIRS
        END IF
        CALL ELEASTEXP(TRANS,EPD,NMP,1,1.0,ERATE,AMP,COFF,DERATE,
1    DAMP,DCOFF,200)
        AMP(1)=AMP(1)
        DAMP(1)=DAMP(1)
        TE=COFF**2.0
        DTE=2*COFF*DCOFF
        TO=(AMP(1)+COFF)**2.0
        DTO=2*(AMP(1)+COFF)*(DAMP(1)-DCOFF)
        WRITE(CTE,'(1PE10.3)') TE
        WRITE(CTO,'(1PE10.3)') TO
        WRITE(CERATE,'(1PE10.3)') ERATE(1)
        WRITE(CDTE,'(1PE10.3)') DTE
        WRITE(CDTO,'(1PE10.3)') DTO
        WRITE(CDERATE,'(1PE10.3)') DERATE(1)
        TXT(54,ISET10)='Te = '//CTE
        TXT(55,ISET10)='To = '//CTO
        TXT(56,ISET10)='A = '//CERATE
        TXT(57,ISET10)='dTe = '//CDTE
        TXT(58,ISET10)='dTo = '//CDTO
        TXT(59,ISET10)='dA = '//CDERATE
        TXT(60,ISET10)='T = (Te**0.5+(To**0.5-Te**0.5)**-AX)**2.0'
        SLOPE=ERATE(1)
        YINT=TO
        OFFSET=TE
      END IF
      IFUN=9
      CALL LLLNIN(8)
      CALL PLOTFUN(ISET,IFUN,CLIPMIN,CLIPMAX,ISET1,ISET2,SLOPE,
1   YINT,OFFSET,NN,AAA)
ELSEIF (CHOICE.EQ.'F') THEN
   CALL CORBOX(ISET,CORAY,NPAIRS,ILINDEX,INC,IFLG,CLIPMIN,
1   CLIPMAX,ISET1,ISET2,1,IGIN,IDIAMETER)
 ELSEIF (CHOICE.EQ.'G') THEN
   CALL CORBOX(ISET,CORAY,NPAIRS,ILINDEX,INC,IFLG,CLIPMIN,
1   CLIPMAX,ISET1,ISET2,2,IGIN,IDIAMETER)
 ELSEIF (CHOICE.EQ.'H') THEN
   WRITE(*,'('''S    COLOR INDEX TO FIT LINE TO: '')')
   READ(*,*) ICOL
```

```
      CALL CORFIT(ISET,CORAY,NPAIRS,ICOL,TXT,ILSEG,ISET10,ISET1,
1    ISET2,CLIPMIN,CLIPMAX,SLOPE,YINT,NN,AAA,ICLRS)
    ELSEIF (CHOICE.EQ.'I') THEN
      CALL SUBCOR(NPAIRS,CORAY,TXT,ISET10)
    ELSEIF (CHOICE.EQ.'J') THEN
      CALL ADDTEXT(TXT,ISET10,IGIN)
    ELSEIF (CHOICE.EQ.'K') THEN
      TITLE=DATANAME(ISET2)//' vs '//DATANAME(ISET1)
      CALL AXESMENU(CLIPMIN(ISET1),CLIPMAX(ISET1),CLIPMIN(ISET2),
1    CLIPMAX(ISET2),IXBIGTICS(ISET1),IXBIGTICS(ISET2),
1    IXTICS(ISET1),IXTICS(ISET2),IXGRID,IYGRID,IGLINST,IAXISX,
```

What is claimed is:

1. A method for producing a map of whole-wafer etch pit density in a GaAs surface, comprising the steps of:
   a. focusing a light source of a predetermined wavelength at a plurality of points on said GaAs surface;
   b. detecting the fractional transmission (T) of light through said GaAs surface at said plurality of points;
   c. determining the average area (a) of etch pits in said GaAs surface;
   d. determining one reference transmission point ($T_O$) at a location on said GaAs surface having relatively high fractional transmission;
   e. determining one reference transmission point ($T_E$) at a location on said GaAs surface having relatively low fractional transmission; and
   f. generating a map of the etch pit density ($\rho_D$) at each of said plurality of points according to the equation $$\rho_D = -\frac{1}{a} \ln \frac{T^{\frac{1}{2}} - T_E^{\frac{1}{2}}}{T_O^{\frac{1}{2}} - T_E^{\frac{1}{2}}}.$$

2. The method of claim 1, further including the step of determining etch pit density at at least two points on said GaAs surface corresponding with two of said plurality of points in which said fractional transmission (T) is detected.

3. The method of claim 1 wherein said light source has a wavelength of 1.45–1.8 μm.

4. A method for producing a map of etch pit density in a GaAs wafer surface, comprising the steps of:
   a. determining etch pit density ($\rho_D$) at at least two points on said GaAs wafer surface;
   b. focusing a light source of predetermined wavelength at a plurality of points on said GaAs wafer surface;
   c. detecting the fractional transmission (T) of said light source through said GaAs wafer surface at said plurality of points;
   d. selecting two locations on said GaAs surface where one of said at least two points in step a is in common with one of said plurality of points in step c; one of the locations being in an area of said GaAs wafer surface having relatively high transmission and other in an area having relatively low transmission;
   e. determining the average area (a) of etch pits on said GaAs wafer surface;
   f. calibrating a reference transmission point ($T_O$) from the fractional transmission and the etch pit density at one of said two locations in step d where the transmission is high;
   g. calibrating a reference transmission point ($T_E$) from the fractional transmission and etch pit density at the other of said two locations in step d where the transmission is low; and
   h. generating a map of etch pit density ($\rho_D$) at each of said plurality of points according to the equation $$\rho_D = -\frac{1}{a} \ln \frac{T^{\frac{1}{2}} - T_E^{\frac{1}{2}}}{T_O^{\frac{1}{2}} - T_E^{\frac{1}{2}}}.$$

5. The method of claim 4 wherein said light source has a wavelength of 1.45–1.8 μm.

6. A system for producing maps of whole-wafer etch pit density in a GaAs wafer comprising:
   means for generating light of a predetermined wavelength;
   means for focusing said light on a surface of a GaAs wafer under test;
   means for moving said GaAs wafer orthogonally relative to said light source;
   means for detecting the fractional transmission (T) of said light through said GaAs wafer at a plurality of points on the surface thereof.
   manual entry means for entering the location and density of a number of etch pit points on the surface of said GaAs wafer and the average area (a) of each etch pits;
   means for calibrating the detected fractional transmission (T) with at least two manually entered etch pit points from identical locations said last mentioned means including means for generating at least one reference transmission point ($T_O$) in an area of said GaAs wafer having relatively high transmission and means for generating at least one reference transmission point ($T_E$) in an area of said GaAs having relatively low transmission; and
   means for generating a map of the etch pit density ($\rho_D$) at each of said plurality of points according to the equation $$\rho_D = -\frac{1}{a} \ln \frac{T^{\frac{1}{2}} - T_E^{\frac{1}{2}}}{T_O^{\frac{1}{2}} - T_E^{\frac{1}{2}}}.$$

7. The system of claim 6, wherein said means for generating light of a predetermined wavelength comprises a monochromator with tungsten-halide lamp source.

8. The system of claim 6, wherein said light has a predetermined wavelength of 1.45–1.8 μm.

9. The system of claim 8, wherein said means for focusing said light on said surface of said GaAs wafer under test comprises an optical lens.

10. The system of claim 7, wherein said means for moving said GaAs wafer orthogonally relative to said light source comprises a computer controlled X-Z drive apparatus.

11. The system of claim 10, wherein said means for detecting the fractional transmission (T) of said light through said GaAs wafer at a plurality of points comprises a cooled germanium detector coupled to a readout amplifier.

* * * * *

UNITED STATES PATENT AND TRADEMARK OFFICE
CERTIFICATE OF CORRECTION

PATENT NO. : 5,008,542

DATED : April 16, 1991

INVENTOR(S) : David C. Look et al

It is certified that error appears in the above-identified patent and that said Letters Patent is hereby corrected as shown below:

```
On the title page:
Abstract, line 2, "etch" should read --etched--.
Col 1, line 42, "lo" should read --10--.
Col 1, line 54, "cf" should read --of--.
Col 1, line 54, a comma chould follow "wafer".
Col 1, line 62, a period should follow "circuit".
Col 3, line 20, "Pair" should read --pair--.
Col 4, line 1, the period following "AE" should be a comma.
Col 24, line 34, "each" should read --said--.
Col 24, line 37, a comma should follow "locations".
Cols 21-24, the computer program text beginning with
"WRITE(3,*)IREGIONS,2" and ending with "1 IXTICS(ISET1),IXTICS
(ISET2),IXGRID,IYGRID,IGLINST,IAXISXK," should properly appear
in Col 11 following "OPEN(UNIT=3,FILE=;WAFEX.DAT',STATUS='NEW')"
```

Signed and Sealed this

Fifth Day of January, 1993

*Attest:*

DOUGLAS B. COMER

*Attesting Officer*     Acting Commissioner of Patents and Trademarks